(12) United States Patent
Gao et al.

(10) Patent No.: US 8,709,406 B2
(45) Date of Patent: *Apr. 29, 2014

(54) PREVENTION AND TREATMENT OF OXIDATIVE STRESS DISORDERS BY GLUTHATHIONE AND PHASE II DETOXIFICATION ENZYMES

(71) Applicant: Brassica Foundation for ChemoProtection Research, Baltimore, MD (US)

(72) Inventors: Xiangqun Gao, Joppa, MD (US); Albena T. Dinkova-Kostova, Baltimore, MD (US); Paul Talalay, Baltimore, MD (US)

(73) Assignee: Brassica Foundation for Chemoprotection Research, Inc., Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/670,161

(22) Filed: Nov. 6, 2012

(65) Prior Publication Data
US 2013/0157965 A1 Jun. 20, 2013

Related U.S. Application Data

(62) Division of application No. 12/179,986, filed on Jul. 25, 2008, now Pat. No. 8,303,949, which is a division of application No. 10/499,196, filed as application No. PCT/US02/40457 on Dec. 18, 2002, now Pat. No. 7,407,986.

(60) Provisional application No. 60/340,273, filed on Dec. 18, 2001.

(51) Int. Cl.
A61K 38/44 (2006.01)

(52) U.S. Cl.
USPC .......................................... 424/94.4; 435/183

(58) Field of Classification Search
USPC .......................................... 424/94.4; 435/183
See application file for complete search history.

(56) References Cited

U.S. PATENT DOCUMENTS

| | | | |
|---|---|---|---|
| 5,411,986 | A | 5/1995 | Cho et al. |
| 5,747,459 | A | 5/1998 | Rowe et al. |
| RE36,784 | E | 7/2000 | Cho et al. |
| 6,159,500 | A | 12/2000 | Demopoulos et al. |
| 6,495,170 | B1 | 12/2002 | Smit et al. |
| 8,303,949 | B2 * | 11/2012 | Gao et al. ............ 424/94.4 |
| 2003/0091518 | A1 | 5/2003 | Pauly et al. |
| 2009/0247477 | A1 | 10/2009 | Talalay |

FOREIGN PATENT DOCUMENTS

| | | |
|---|---|---|
| CN | 1469711 A | 1/2004 |
| EP | 0655245 A2 | 5/1995 |
| JP | 11 124311 A | 5/1999 |
| WO | WO 99/04747 A2 | 2/1999 |
| WO | WO 99/47133 A1 | 9/1999 |
| WO | WO 01/37788 A1 | 5/2001 |
| WO | WO 01/45661 A2 | 6/2001 |
| WO | WO 01/85142 A1 | 11/2001 |
| WO | WO 02/15722 A2 | 2/2002 |

OTHER PUBLICATIONS

Cai, et al., "Oxidative damage and protection of the RPE", Progress in Retinal and Eye Research, vol. 19, No. 2, 2000, pp. 205-221.
Carmody, et al., "Reactive Oxygen Species as Mediators of Photoreceptor Apoptosis in Vitro", Experimental Cell Research, vol. 248, 1999, pp. 520-530.
Christen, et al., "Antioxidants and Eye Disease", The American Journal of Medicine, vol. 97 (suppl 3A), 1994, pp. 3A-14S-3S-17S.
Partial European Search Report received in the related EP case EP 09172558 dated Feb. 15, 2010.
Translation of Japanese Office Action from corresponding Japanese Patent Application No. 2003-552246, dated Jan. 27, 2009. (3 pgs.).
Fahey et al., "Antioxidant Functions of Sulforaphane: a Potent Inducer of Phase II Detoxication Enzymes,"Food and Chemical Toxicology, vol. 37, Elsevier Science Ltd., GB, 1999, pp. 973-979.
Fahey et al., "Broccoli Sprouts: An Exceptionally Rich Source of Inducers of Enzymes that Protect Against Chemical Carcinogens," Proc. Natl. Acad. Sci., vol. 94, Sep. 16, 1997, USA, pp. 10367-10372.
Fahey et al., "The Chemical Diversity and Distribution of Glucosinolates and Isothiocyanates Among Plants," Photochemistry, vol. 56, Elsevier Science Ltd., 2000, pp. 5-51.
Favreau, et al., J. Biol. Chem. 266: 4556-4561 (1991).
Gao et al., "Powerful and prolonged protection of human retinal pigment epithelial cells, keratinocytes, and mouse leukemia cells against oxidative damage: the indirect antioxidant effects of sulforaphane," Proceedings of the National Academy of Sciences of the United States of America, vol. 98, No. 26, Dec. 18, 2001, p. 15221, XP002392650.
Harman, "Free radical theory of ageing: Applications," The Asia Pacific Heart Journal, vol. 7, No. 3, Dec. 11998, pp. 169-177, XP004886293.
Jakoby et al., "The enzymes of detoxication," The Journal of Biological Chemistry, vol. 265, No. 34, 1990, pp. 20715-20718, XP002392651.
Mulcahy et al., "Constitutive and B-Naphthoflavone-induced Expression of the Human Y-Glutamylcysteine Synthetase Heavy Subunit Gene Is Regulated by a Distal Antioxidant Response Element/TRE Sequence," J. Biol. Chem., vol. 272, Mar. 14, 1997, pp. 7445-7454.
Nelson et al., "Effect of Dietary Inducer Dimethylfumarate on Glutathione in Cultured Human Retinal Pigment Epithelial Cells", Investigative Ophhthalmology & Visual Science, Aug. 1999, vol. 40, No. 9, pp. 1927-1935.

(Continued)

Primary Examiner — Tekchand Saidha
(74) Attorney, Agent, or Firm — Foley & Lardner LLP

(57) ABSTRACT

The present invention generally relates to the field of treating oxidative stress disorders by administering a pharmaceutically effective amount of a compound that elevates the intracellular levels of glutathone or intracelluar levels of at least one Phase II detoxification enzyme in animal tissue. The present invention also relates to the field of protecting a subject from oxidative stress disorders by administering a pharmaceutically effective amount of a compound that elevates the intracellular levels of glutathone or intracelluar levels of at least one Phase II detoxification enzyme in the subject. The present invention also relates to a pharmaceutical composition useful for the treatment of oxidative stress disorders.

14 Claims, 6 Drawing Sheets

(56) References Cited

OTHER PUBLICATIONS

Prochaska, et al., Oxidative Stress: Oxidants and Antioxidants, 195-211 (1991).

Smith et al., "Effects of the Antioxidant Butylated Hydroxytoluene (BHT) on Retinal Degenration Induced Transplacentally by a Single Low Dosage of N-Methyl-N-Nitrosourea (MNU)", Teratogenesis, Carcinogenesis, and Mutagenesis 8:175-189 (1988).

Thimmulappa et al., "Identification of Nrf2-regulated Genes Induced by the Cemopreventive agent Sulforaphane by Oligonucleotide Microarray," *Cancer Research*, vol. 62, Sep. 15, 2002, pp. 5196-5203.

Verna et al., "UVA-induced oxidative damage in retinal pigment epithelial cells after $H_2O_2$ or sparfloxacin exposure", Cell Biology and Toxicology, 2000:16, pp. 303-312.

Wally et al., Food and Chemical Toxicology 36 (1998): 365-373.

Winkler et al., "Oxidative damage and age-related macular degeneration", Molecular Vision 1999; 5:31, pp. 1-11.

Zhang et al., "A Major Inducer of Anticarcinogenic Protective Enzymes from Broccoli: Isolation and Elucidation of Structure," *Proc. Natl. Acad. Sci.*, vol. 89, USA, Mar. 15, 1992, pp. 2399-2403.

Zhang et al., "Anticarcinogenic Activities of Sulforaphane and Structurally Related Synthetic Norbornyl Isothiocyanates," *Proc. Natl. Acad. Sci.*, vol. 91, USA, Apr. 12, 1994, pp. 3147-3150.

Summons to attend oral proceedings received the related European Patent Application No. EP 09172558.0, dated Feb. 28, 2013.

Sata, et al., "Menodione induces both necrosis and apoptosis in rat pancreatic acinar ar4-2j cells", Free Radical Biology & Medicine, 1997, vol. 23, No. 6. pp. 844-850.

\* cited by examiner

PREVENTION AND TREATMENT OF OXIDATIVE STRESS DISORDERS BY GLUTHATHIONE AND PHASE II DETOXIFICATION ENZYMES

CROSS-REFERENCE TO RELATED APPLICATION

This application is a divisional application of U.S. patent application Ser. No. 12/179,986, filed on Jul. 25, 2008, now U.S. Pat. No. 8,303,949, which is a divisional application of U.S. patent application Ser. No. 10/499,196, now U.S. Pat. No. 7,407,986, filed as PCT Application No. PCT/US02/40457, on Dec. 18, 2002, all of which are hereby incorporated herein by reference.

The present application claims priority to U.S. provisional application Ser. No. 60/340,273, filed on Dec. 18, 2001, which is incorporated herein by reference.

FIELD OF THE INVENTION

The present invention generally relates to the field of treating oxidative stress by administering a pharmaceutically effective amount of a compound that elevates intracellular levels of glutathione or intracellular levels of at least one Phase II detoxification enzyme in animal cells. The present invention also relates to the field of protecting a subject from oxidative stress by administering a pharmaceutically effective amount of a compound that elevates intracellular levels of glutathione or intracellular levels of at least one Phase II detoxification enzyme in animal cells. The present invention also relates to a pharmaceutical composition useful for the treatment of an oxidative stress disorder.

BACKGROUND OF THE INVENTION

The toxicity of oxygen and more specifically its partial reduction products known as reactive oxygen species (ROS) is commonly designated as oxidative stress. It arises from an imbalance of cellular pro-oxidant and antioxidant processes. Oxidative stress has been implicated in a variety of pathological and chronic degenerative processes including the development of cancer, atherosclerosis, inflammation, aging, neurodegenerative disorders, cataracts, retinal degeneration, drug action and toxicity, reperfusion injury after tissue ischemia, and defense against infection. See, for instance, Gao X, Dinkova-Kostova A T, Talalay P. (2001) Proc Natl Acad Sci USA., 98(26):15221-6, which is incorporated herein by reference. The publications listed at page 15226 of Gao et al., 2001, supra, also are incorporated herein by reference. Mammalian cells contribute to their own oxidative stress by generating ROS as part of normal aerobic metabolism, and have developed elaborate and overlapping mechanisms for combating these hazards (Halliwell, B. & Gutteridge, J. M. C. (1999) *Free Radicals in Biology and Medicine*. Oxford University Press, New York, pp. 1-36). Nevertheless, protective mechanisms are not completely effective especially during increased oxidative stress. The desirability of developing methods for augmenting these defenses is reflected in the widespread human consumption and perceived health benefits of plant-based antioxidants such as ascorbic acid, tocopherols, carotenoids, and polyphenols (Pokorny, J., Yanishlieva, M. & Gordon, M. (2001) *Antioxidants in food: practical applications*. Woodhead Publishing, Ltd., Cambridge, U.K). These direct antioxidants neutralize free radicals and other chemical oxidants but are consumed in these reactions. Additional compounds are needed to protect subjects from oxidative stress disorders as well as for treatment of subjects suffering from these same disorders.

SUMMARY OF THE INVENTION

The invention relates to a method of treating a subject in need of treatment of an oxidative stress disorder, which comprises administering to the subject a pharmaceutically effective amount of a compound that elevates glutathione, or at least one Phase II detoxification enzyme, in the diseased tissue of the subject. The compound may be an isothiocyanate such as sulforaphane, or a glucosinolate. The oxidative stress disorder may be retinal degeneration, Alzheimer's Disease or aging. The Phase II detoxification enzyme may be UDP-glucuronosyltransferases, sulfotransferases, phenol-O-methyltransferase, catechol-O-methyltransferase, histamine N-methyltransferase, nicotinamide N-methyltransferase, thiopurine methyltransferase, thiol methyltransferase, N-acetyltransferases, O-acetyltransferases, acyl-CoA synthetases, acyl-CoA:amino acid N-acyltransferases, aminoacyl-tRNA synthetases, glutathione synthetases, gamma glutamylcysteine synthetases, glutathione S-transferases, quinone reductases, heme oxygenases, rhodaneses, glutathione reductase, glutathione peroxidase, catalase and superoxide dismutase. The invention relates to a method of protecting a subject from oxidative stress disorder, which comprises administering to the subject a pharmaceutically effective amount of a compound that elevates glutathione, or at least one Phase II detoxification enzyme, in the cells of the subject. The compound may be an isothiocyanate such as sulforaphane, or a glucosinolate. The oxidative stress disorder may be retinal degeneration, Alzheimer's Disease or aging. The Phase II detoxification enzyme may be UDP-glucuronosyltransferases, sulfotransferases, phenol-O-methyltransferase, catechol-O-methyltransferase, histamine N-methyltransferase, nicotinamide N-methyltransferase, thiopurine methyltransferase, thiol methyltransferase, N-acetyltransferases, O-acetyltransferases, acyl-CoA synthetases, acyl-CoA:amino acid N-acyltransferases, aminoacyl-tRNA synthetases, glutathione synthetases, gamma glutamylcysteine synthetases, glutathione S-transferases, quinone reductases, heme oxygenases, rhodaneses, glutathione reductase, glutathione peroxidase, catalase and superoxide dismutase.

The invention relates to a method of protecting a subject from ocular degeneration, which comprises administering to the subject a pharmaceutically effective amount of a compound that elevates intracellular levels of glutathione or intracellular levels of at least one Phase II detoxification enzyme in diseased tissue of said subject. The compound may be an isothiocyanate such as sulforaphane, or a glucosinolate. The oxidative stress disorder may be retinal degeneration, Alzheimer's Disease or aging. The Phase II detoxification enzyme may be UDP-glucuronosyltransferases, sulfotransferases, phenol-O-methyltransferase, catechol-O-methyltransferase, histamine N-methyltransferase, nicotinamide N-methyltransferase, thiopurine methyltransferase, thiol methyltransferase, N-acetyltransferases, O-acetyltransferases, acyl-CoA synthetases, acyl-CoA:amino acid N-acyltransferases, aminoacyl-tRNA synthetases, glutathione synthetases, gamma glutamylcysteine synthetases, glutathione S-transferases, quinone reductases, heme oxygenases, rhodaneses, glutathione reductase, glutathione peroxidase, catalase and superoxide dismutase.

Similarly, the present invention also relates to a method of protecting a subject from photooxidation, comprising administering to a subject a pharmaceutically effective amount of a compound that elevates intracellular levels of glutathione or intracellular levels of at least one Phase II detoxification enzyme in a tissue of said subject. The subject's tissue may be skin, or an ocular organ, such as the eye.

The invention also relates to a composition for use in the treatment of a oxidative stress disorder, which comprises a pharmaceutical excipient and a pharmaceutically effective amount of an agent that increases intracellular levels of glutathione or at least one Phase II detoxification enzyme.

DETAILED DESCRIPTION OF THE PREFERRED EMBODIMENTS

Figure 1:
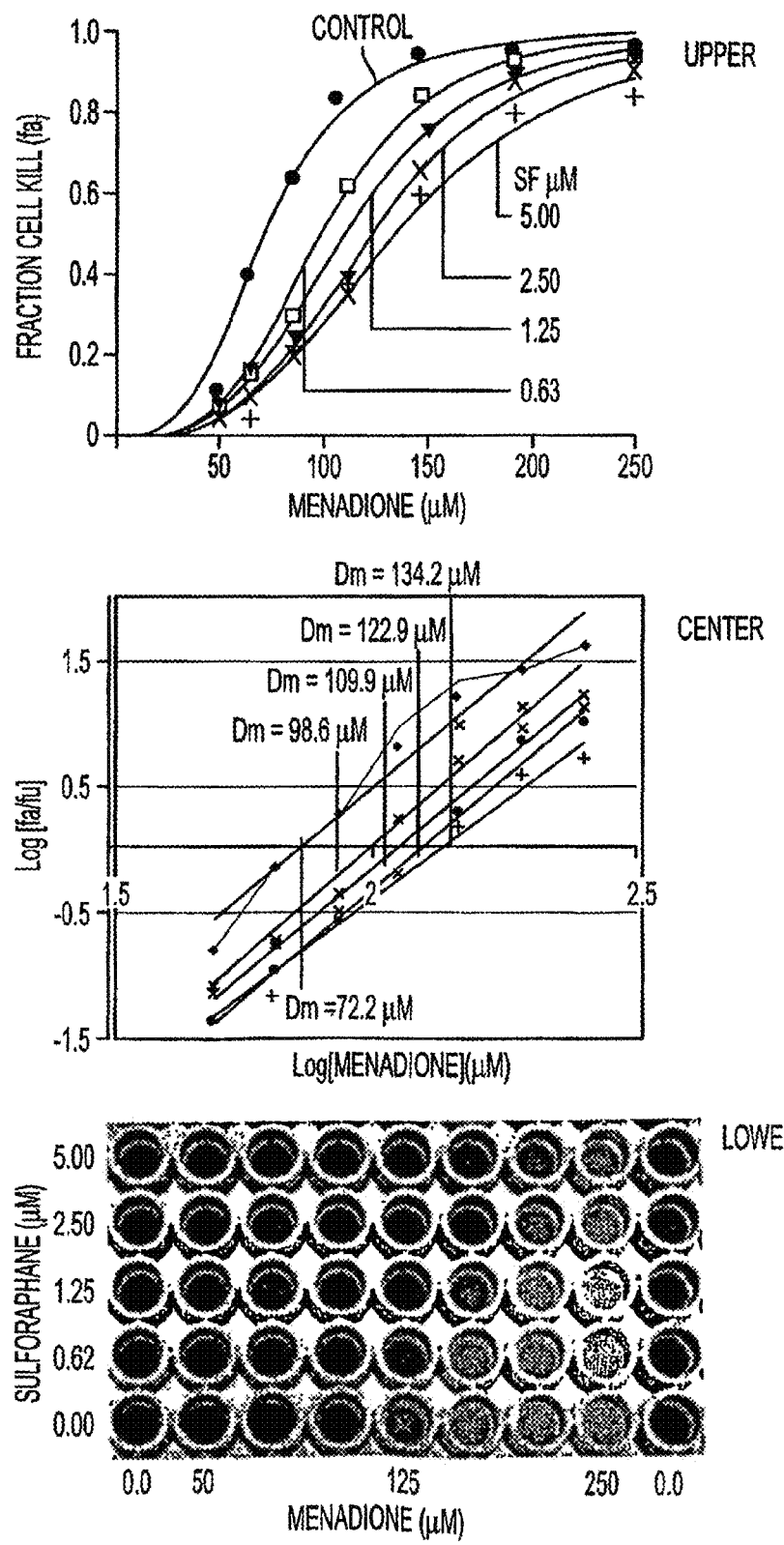
FIG. 1. Protection of adult human retinal pigment epithelial (ARPE-19) cells against the toxicity of menadione (0-250 µM) by induction of Phase 2 enzymes by sulforaphane (0-5 µM). Upper, Fractional killing of cells ($f_a$) as a function of menadione concentration at a series of sulforaphane concentrations. Center, Analysis of the data by the median effect plot. The median effect concentrations ($D_m$) at the above sulforaphane concentrations is shown. For sulforaphane concentrations 5.00, 2.50, 1.25 and 0.63 µM, the $D_m$ value is 134.2, 122.9, 109.9 and 98.6 µM, respectively. Lower, Photograph of a typical 96-well microtiter plate showing the protective effect of sulforaphane against the cytotoxicity of menadione for human ARPE-19 cells. The intensity of purple color is the reduced MIT formazan for a measure of cell viability.

The present invention relates to a method of treating a subject in need of treatment of an oxidative stress disorder, the method comprising administering to the subject a pharmaceutically effective amount of a compound that elevates levels intracellular glutathione or intracellular levels of at least one Phase II detoxification enzyme in diseased tissue of said subject.

Many human chronic diseases are related to oxidative stress, but in some anatomical locations this oxidative stress is aggravated by light or irradiation. One common "anatomical location" is the skin, where ultraviolet light is a causative agent for skin cancer. Another example is constant damage in the retina of the eye by the retinal molecules involved in the visual cycle. These polyunsaturated substances can act as oxidants (i.e., "photooxidants") and their ability to produce reactive oxygen species is markedly enhanced by UV light of the appropriated wavelength. We therefore studied whether the cytotoxic effect of all-trans-retinal in combination with UV light could be abrogated by induction of phase 2 enzymes by sulforaphane. Example 6, described below, illustrates this protective function. In this respect, the present invention contemplates the abrogation of any cytotoxic effect induced by retinal metabolic products, derivatives, or variants thereof, such as "cis-retinal" (e.g., the 11-cis-retinal isoform), in combination with light, especially UV light, as prescribed by the present invention.

As used herein, the term subject can be used to mean an animal, preferably a mammal, including a human or non-human. The term patient is used to indicate a subject in need of treatment of an oxidative stress disorder. The terms "disease," "condition" and "disorder" may all be used interchangeably.

The current invention can be useful in treating a subject in need of treatment of an oxidative stress disorder where there may be aberrant levels of glutathione or any Phase II enzyme present in the diseased cells or tissue. These abnormal levels may be either causal or symptomatic of the oxidative stress disorder. The phrase "oxidative stress disorder," as used in the current context, arises from an imbalance of cellular pro-oxidant and antioxidant processes resulting in cell death. Oxidative stress has been implicated in a variety of pathological and chronic degenerative processes including the development of cancer, atherosclerosis, inflammation, aging, neurodegenerative disorders, cataracts, retinal degeneration, drug action and toxicity, reperfusion injury after tissue ischemia, and defense against infection.

The treatment envisioned by the current invention can be used for patients with a pre-existing oxidative stress disorder, or for patients pre-disposed to an oxidative stress disorder. Additionally, the method of the current invention can be used to correct cellular or physiological abnormalities involved with an oxidative stress disorder in patients.

As used herein, the term agent or compound is intended to mean any chemical that elevates intracellular levels of glutathione or Phase II enzymes.

As used herein, "a pharmaceutically effective amount" is intended used to mean an amount effective to elicit a cellular response that is clinically significant, without excessive levels of side effects.

The present invention relates to methods of elevating intracellular glutathione (GSH) as a way to prevent or treat oxidative stress disorders. GSH is a tripeptide composed of glycine, cysteine and glutamate, with the glutamate being linked to cysteine via the gamma-carboxyl group (as opposed to an alpha-carboxyl linkage that normally occurs is in a peptide). GSH is a detoxifying peptide that the body conjugates to xenobiotics (foreign chemical or compound) to render the xenobiotic more hydrophilic, thus promoting their excretion from the body. The synthesis of GSH involves a two-step reaction, with the first being catalyzed by gamma-glutamylcysteine synthetase. Glutathione synthetase catalyzes the second reaction. In turn, the conjugation of GSH to the xenobiotic is catalyzed by glutathione S-transferase (also referred to as GSH transferase), which can be a dimer of identical (homodimer) or different (heterodimer) subunits, although some heterodimers do exist. To date, at least four classes of GSH transferases have been identified, with each class having two or more types of subunits therein. Most GSH transferases are cytosolic (or soluble), meaning they are found in a cell's cytosol, although at least two microsomal GSH transferases exist. Based on such factors as amino acid similarity and biological activity, one of ordinary skill in the art will be able to appreciate and recognize the many types of GSH transferases that exist, as well as any that may not yet be identified. Thus, as used herein, the phrases "increase in intracellular GSH" or "elevation in intracellular GSH" is intended to mean the GSH tripeptide itself, as well as the enzymes responsible for its synthesis and conjugation to xenobiotics.

The present invention also relates to a method increasing the intracellular levels of at least one Phase II detoxification enzyme. The phrases "Phase II detoxification enzyme" and "Phase II enzyme" are used interchangeably herein. As used herein, a Phase II enzyme is any enzyme that is involved in any of the Phase II reactions which are responsible for the biotransformation of xenobiotics and/or prevention of oxidative stress. Generally speaking, a Phase II reaction will generally involve the conjugation of a moiety to the xenobiotic that will increase the hydrophilicity of the xenobiotic. This conjugated xenobiotic, which is now more hydrophilic, is more readily excreted from the body, than the unconjugated xenobiotic. There are six types of Phase II conjugation reactions, including glucuronidation, sulfation, methylation, acetylation, amino acid conjugation and glutathione conjugation. The reaction catalyzed by the enzyme rhodanese (the transfer of a sulfur ion to cyanide to form thiocyanate) will also be considered a Phase II reaction herein.

Briefly, glucuronidation is a major pathway of xenobiotic transformation and involves the conjugation of glucuronide to the xenobiotic. The reaction is catalyzed by UDP-glucuronosyltransferase (UDPGT), of which multiple forms exist. These multiple forms are encoded by several different genes. One of ordinary skill in the art will be able to recognize and appreciate the different forms of UDPGT, and the reactions they catalyze.

Sulfation is a pathway of xenobiotic transformation that involves the conjugation of sulfate to the xenobiotic. The reaction is catalyzed by sulfotransferases, of which more than a dozen forms have been identified. One of ordinary skill in the art will be able to recognize and appreciate the different forms of sulfotransferases, and the reactions they catalyze.

Methylation is a pathway of xenobiotic transformation that involves the conjugation of a methyl group to the xenobiotic. There are three different methylation reactions, based on the type of atom on the xenobiotic that is methylated. The three methylation reactions can occur on, sulfur (S), oxygen (O) and nitrogen (N), each of which is catalyzed by a different sets of enzymes. O-methylation is catalyzed by phenol-O-methyltransferase (POMT) or catechol-O-methyltransferase (COMT). It is believed that COMT is encoded by a single gene, with at least two different allelic variants. N-methylation is catalyzed by histamine-N-methyltransferase or nicotinamide-N-methyltransferase. S-methylation is catalyzed by at least two enzymes, including thiopurine methyltransferase (TPMT) and thiol methyltransferase (TMT). One of ordinary skill in the art will be able to recognize and appreciate the different forms of methlytransferases, and the reactions they catalyze.

Acetylation is a pathway of xenobiotic transformation that involves the conjugation of an acetyl group to the xenobiotic. There are two different acetylation reactions, based on the type of atom (O and N) on the xenobiotic that is acetylated. The two acetylation reactions may or may not be catalyzed by the same set of enzymes. N-acetylation is catalyzed by N-acetyltransferase (NAT), of which two forms exist in humans. These forms are encoded by two different genes. O-acetylation is catalyzed by O-acetyltransferase, but may also be catalyzed by NAT. One of ordinary skill in the art will be able to recognize and appreciate the different forms of acetyltransferases, and the reactions they catalyze.

Amino acid conjugation is a pathway of xenobiotic transformation that involves the conjugation of an amino acid to the xenobiotic. There are two principle pathways where amino acids are conjugated to xenobiotics. The first reaction involves xenobiotics containing a carboxylic acid. This reaction takes place by acyl-CoA synthetase catalyzing the conjugation of CoA to the xenobiotic to form a thioester. The thioester is subsequently conjugated to the amino acid via the acyl-CoA: amino acid N-transferase enzyme. The second principle pathway where xenobiotics are conjugated to amino acids involves xenobiotics containing an aromatic hydroxylamine. This reaction involves the activation of an amino acid with the aminoacyl-tRNA-sythetase. The activated amino acid subsequently reacts with the aromatic hydroxylamine on the xenobiotic to form a reactive N-ester. One of ordinary skill in the art will be able to recognize and appreciate the different types of enzymes responsible for the conjugation of amino acids to xenobiotics, and the reactions they catalyze.

Quinone reductase (QR) is considered a Phase II enzyme because it has protective functions (Prochaska, et al., Oxidative Stress: Oxidants and Antioxidants, 195-211 (1991)), is induced coordinately with other phase II enzymes, and is regulated by enhancer elements similar to those that control glutathione transferase (Favreau, et al., J. Biol. Chem. 266: 4556-4561 (1991)).

Heme oxygenase (HO), also considered a Phase II enzyme, catalyzes the conversion of heme to biliverdin, which is subsequently reduced to bilirubin. Thus the HO enzyme is responsible for the production of bilirubin, which itself is a powerful antioxidant. Additionally, the HO enzyme is induced by many of the same compounds that induce other Phase II enzymes.

Examples of additional Phase II enzymes include, but are not limited to, such enzymes as glutathione reductase, glutathione peroxidase, catalase and superoxide dismutase.

The present invention relates to increasing the levels of at least one Phase II enzyme in diseased tissue. It is possible that the compounds contemplated in this invention may be responsible for the increased levels of only one of the Phase II enzymes, or more than one Phase II enzyme. As used herein, the phrase "increase in levels of Phase II enzymes" is used to mean an increase in the quantity of Phase II enzymes present in the cell, compared to control (non-stimulated) levels. The phrase is also used to mean an increase in the activity or specificity of the enzymes present in the cell.

As used herein, the term diseased tissue may be used to mean individual cells, as cultured in vitro, or excised tissue in whole or in part. Diseased tissue may also be used to mean tissue in the subject that is undergoing the degenerative process, or tissue within the same organ that may not yet be affected by the degenerative process. The normal tissue may or may not be adjacent to the degenerative tissue.

As a preferred embodiment, the compounds used in the methods of the current invention that elevate glutathione or any Phase II enzyme, are selected from the group consisting of an isothiocyanate and a glucosinolate.

Isothiocyanates are compounds containing the thiocyanate (SCN) moiety and are easily identifiable by one of ordinary skill in the art. An example of an isothiocyanate includes, but is not limited to sulforaphane or its analogs. The description and preparation of isothiocyanate analogs is described in U.S. Reissue Pat. No. 36,784, and is hereby incorporated by reference in its entirety. In a preferred embodiment, the sulforaphane analogs used in the present invention include 6-isothiocyanato-2-hexanone, exo-2-acetyl-6-isothiocyanatonorbornane, exo-2-isothiocyanato-6-methylsulfonylnorbornane, 6-isothiocyanato-2-hexanol, 1-isothiocyanato-4-dimethylphosphonylbutane, exo-2-(1'-hydroxyethyl)-5-isothiocyanatonorbornane, exo-2-acetyl-5-isothiocyanatonorbornane, 1-isothiocyanato-5-methylsulfonylpentane, cis-3-(methylsulfonyl)cyclohexylmethylisothiocyanate and trans-3-(methylsulfonyl)cyclohexylmethylisothiocyanate.

Glucosinolates, which are well-known in the art, are precursors to isothiocyanates. Glucosinolates are easily recognizable and appreciated by one of ordinary skill in the art and are reviewed in Fahey et al. Phytochemistry, 56:5-51 (2001), the entire contents of which are hereby incorporated by reference.

Other compounds contemplated by the present invention include compounds that are known to induce (increase) levels of Phase II enzymes. Preferably, these compounds include resveratrol, oltipraz, dimethylfumarate, 2(3)-tert-butyl-4-hydroxyanisole, 3,5-di-tert-butyl-4-hydroxytoluene and an analog thereof.

As used herein, the phrase "increased or decreased expression" is used to mean an increase or decrease in the transcription rates of the genes responsible for coding the enzymes, resulting in an increase or decrease in the levels of mRNA for each gene, respectively. The phrase is also used to mean an increase or decrease in the levels of the protein or enzyme in the cell, independent of transcription rates. For example, an increase in degradation rate of an mRNA encoding the protein in question, without a change in the transcription rate, may result in a decrease in the levels of protein in the cell.

The current invention also provides for a composition for use in the treatment of an oxidative stress disorder, comprising a pharmaceutical excipient and a pharmaceutically effective amount of an agent that increases intracellular levels of glutathione or at least one Phase II detoxification enzyme.

In a preferred embodiment, the composition of the current invention comprises an agent selected from the group consisting of an isothiocyanate and a glucosinolate. In a more preferred embodiment, the composition of the current invention comprises sulforaphane or a sulforaphane analog.

In another preferred embodiment, the composition of the current invention comprises an agent selected from the group consisting of 6-isothiocyanato-2-hexanone, exo-2-acetyl-6-isothiocyanatonorbornane, exo-2-isothiocyanato-6-methylsulfonylnorbornane, 6-isothiocyanato-2-hexanol, 1-isothiocyanato-4-dimethylphosphonylbutane, exo-2-(1'-hydroxyethyl)-5-isothiocyanatonorbornane, exo-2-acetyl-5-isothiocyanatonorbornane, 1-isothiocyanato-5-methylsulfonylpentane, cis-3-(methylsulfonyl)cyclohexylmethylisothiocyanate and trans-3-(methylsulfonyl)cyclohexylmethylisothiocyanate.

In still another preferred embodiment, the composition of the current invention comprises an agent selected from the group consisting of resveratrol, oltipraz, dimethylfumarate, 2(3)-tert-butyl-4-hydroxyanisole, 3,5-di-tert-butyl-4-hydroxytoluene and an analog thereof.

In another preferred embodiment, the composition of the current invention, which is used to treat degenerative diseases by increasing the levels of glutathione or any Phase II enzyme, is used to increase the enzymes selected from the group consisting of UDP-glucuronosyltransferases, sulfotransferases, phenol-O-methyltransferase, catechol-O-methyltransferase, histamine N-methyltransferase, nicotinamide N-methyltransferase, thiopurine methyltransferase, thiol methyltransferase, N-acetyltransferases, acyl-CoA synthetases, acyl-CoA:amino acid N-acyltransferases, aminoacyl-tRNA synthetases, glutathione synthetases, gamma glutamylcysteine synthetases, glutathione S-transferases, quinone reductases, heme oxygenases and rhodaneses.

Formulations and Methods of Administration

A pharmaceutical composition of the invention is provided comprising an agent of the invention useful for treatment of an oxidative stress disorder and a pharmaceutically acceptable carrier or excipient. Such an agent may be artificially synthesized or may be obtained from a naturally occurring source. If the agent is obtained from a naturally occurring source it may not be necessary to combine such agent with a pharmaceutically acceptable carrier or excipient. An exemplary naturally occurring source is *Brassica oleracea* seeds selected from the group of varieties consisting of acephala, alboglabra, *botrytis*, costata, gemmifera, gongylodes, italica, medullosa, palmifolia, ramosa, sabauda, sabellica, and selensia. An additional exemplary naturally occurring source is cruciferous sprouts.

The invention further contemplates the use of prodrugs which are converted in vivo to the therapeutic compounds of the invention (Silverman, R. B., "The Organic Chemistry of Drug Design and Drug Action," Academic Press, Ch. 8 (1992)). Such prodrugs can be used to alter the biodistribution or the pharmacokinetics of the therapeutic compound. For example, an anionic group, e.g., a sulfate or sulfonate, can be esterified, e.g, with a methyl group or a phenyl group, to yield a sulfate or sulfonate ester. When the sulfate or sulfonate ester is administered to a subject, the ester is cleaved, enzymatically or non-enzymatically, to reveal the anionic group. Such an ester can be cyclic, e.g., a cyclic sulfate or sultone, or two or more anionic moieties can be esterified through a linking group. An anionic group can be esterified with moieties (e.g., acyloxymethyl esters) which are cleaved to reveal an intermediate compound which subsequently decomposes to yield the active compound. Furthermore, an anionic moiety can be esterified to a group which is actively transported in vivo, or which is selectively taken up by target organs. The ester can be selected to allow specific targeting of the therapeutic moieties to particular organs, as described below for carrier moieties.

The pharmaceutical composition can be administered orally, nasally, parenterally, intrasystemically, intraperitoneally, topically (as by drops or transdermal patch), bucally, or as an oral or nasal spray. By "pharmaceutically acceptable carrier" is intended, but not limited to, a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

A pharmaceutical composition of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention can also contain adjuvants such as, but not limited to, preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It can also be desirable to include isotonic agents such as sugars, sodium chloride, and the like. Prolonged absorption of the injectable pharmaceutical form can be brought about by the inclusion of agents which delay absorption such as aluminum monostearate and gelatin.

In some cases, in order to prolong the effect of the drugs, it is desirable to slow the absorption from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include, but are not limited to, capsules, tablets, pills, powders, and granules. In such solid dosage forms, the active compounds are mixed with at least one item pharmaceutically acceptable excipient or carrier such as sodium citrate or dicalcium phosphate and/ or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and I) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hardfilled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include, but are not limited to, pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Administration to the eyes can be any of the many methods well know to those skilled in the art including drops, foams, polymeric compositions, gels, implantable time-release compostions, oral dose forms, injectable dose forms, phase transition forms, ointments, creams, solid implants, among others.

Compositions for topical administration, including those for inhalation, can be prepared as a dry powder which can be pressurized or non-pressurized. In nonpressurized powder compositions, the active ingredients in finely divided form can be used in admixture with a larger-sized pharmaceutically acceptable inert carrier comprising particles having a size, for example, of up to 100 µm in diameter. Suitable inert carriers include sugars such as lactose. Desirably, at least 95% by weight of the particles of the active ingredient have an effective particle size in the range of 0.01 to 10 µm.

Alternatively, the composition can be pressurized and contain a compressed gas, such as nitrogen or a liquefied gas propellant. The liquefied propellant medium and indeed the total composition is preferably such that the active ingredients do not dissolve therein to any substantial extent. The pressurized composition can also contain a surface active agent. The surface active agent can be a liquid or solid nonionic surface active agent or can be a solid anionic surface active agent. It is preferred to use the solid anionic surface active agent in the form of a sodium salt.

Dosaging

One of ordinary skill will appreciate that effective amounts of the agents of the invention can be determined empirically and can be employed in pure form or, where such forms exist, in pharmaceutically acceptable salt, ester or prodrug form. The agents can be administered to a subject, in need of treatment of a neurological disorder, as pharmaceutical compositions in combination with one or more pharmaceutically acceptable excipients. It will be understood that, when administered to a human patient, the total daily usage of the agents or composition of the present invention will be decided by the attending physician within the scope of sound medical judgement. The specific therapeutically effective dose level for any particular patient will depend upon a variety of factors: the type and degree of the cellular response to be achieved; activity of the specific agent or composition employed; the specific agents or composition employed; the age, body weight, general health, sex and diet of the patient; the time of administration, route of administration, and rate of excretion of the agent; the duration of the treatment; drugs used in combination or coincidental with the specific agent; and like factors well known in the medical arts. For example, it is well within the skill of the art to start doses of the agents at levels lower than those required to achieve the desired therapeutic effect and to gradually increase the dosages until the desired effect is achieved.

For example, satisfactory results are obtained by oral administration of the compounds at dosages on the order of from 0.05 to 10 mg/kg/day, preferably 0.1 to 7.5 mg/kg/day, more preferably 0.1 to 2 mg/kg/day, most preferably 0.5 mg/kg/day administered once or, in divided doses, 2 to 4 times per day. On administration parenterally, for example by i.v. drip or infusion, dosages on the order of from 0.01 to 5 mg/kg/day, preferably 0.05 to 1.0 mg/kg/day and more preferably 0.1 to 1.0 mg/kg/day can be used. Suitable daily dosages for patients are thus on the order of from 2.5 to 500 mg p.o., preferably 5 to 250 mg p.o., more preferably 5 to 100 mg p.o., or on the order of from 0.5 to 250 mg i.v., preferably 2.5 to 125 mg i.v. and more preferably 2.5 to 50 mg i.v.

Dosaging can also be arranged in a patient specific manner to provide a predetermined concentration of the agents in the blood, as determined by techniques accepted and routine in the art (HPLC is preferred). Thus patient dosaging can be adjusted to achieve regular on-going blood levels, as measured by HPLC, on the order of from 50 to 1000 ng/ml, preferably 150 to 500 ng/ml.

It will be readily apparent to one of ordinary skill in the relevant arts that other suitable modifications and adaptations to the methods and applications described herein can be made without departing from the scope of the invention or any embodiment thereof.

The following Examples serves only to illustrate the invention, and are not to be construed as in any way to limit the invention.

EXAMPLES

Retinal cells are especially sensitive to oxidative damage (Cai, J., Nelson, K. C., Wu, M., Sternberg, P. & Jones, D. P. (2000) *Prog. Retinal Eye Res.* 19, 205-221, 2000; Winkler, B. S., Boulton, M. E., Gottsch, J. D. & Sternberg, P. (1999) *Molecular Vision* 5, 32-42.). To mimic the types of oxidative stresses that occur physiologically, we selected the following four oxidants: menadione, tert-butyl hydroperoxide, 4-hydroxynonenal, and peroxynitrite. The mechanisms by which these agents evoke oxidative damage, and how cells protect themselves against such damage are quite different, as described below.

In the examples, ARPE-19 cells were treated with sulforaphane, an isothiocyanate isolated from broccoli on the basis of its Phase 2 inducing activity and the most potent naturally occurring Phase 2 enzyme inducer identified to date (Fahey, J. W., Zhang, Y. & Talalay, P. (1997) *Proc. Natl. Acad. Sci. USA* 94, 10367-10372; Zhang, Y., Talalay, P., Cho, C. G. & Posner, G. H. (1992) *Proc. Natl. Acad. Sci. USA* 89, 2399-2403; and Zhang, Y., Kensler, T. W., Cho, C. C., Posner, G. H. & Talalay, P. (1994) *Proc. Natl. Acad. Sci. USA* 91, 3147-3150). Sulforaphane coordinately induces a family of Phase 2 detoxication enzymes and related proteins, and raises GSH levels by inducing γ-glutamylcysteine synthetase, the rate-limiting enzyme in GSH biosynthesis (Mulcahy, R. T., Wartman, M. A., Bailey, H. H. & Gipp, J. J. (1997) *J. Biol. Chem.* 272, 7445-7454).

Cell viability measurements were analyzed by the median effect equation of Chou and Talalay, (1984) *Adv. Enzyme Regul.* 22, 27-55, in order to obtain the median effect concentration ($D_m$) based on all the data points of the cytotoxicity-concentration curves. The $D_m$ value for each oxidant was then compared to that for cells that had been treated with a range of concentrations of sulforaphane, thereby generating quantitative measures of protection.

Sulforaphane cannot react directly with free radicals or ROS: its "antioxidant" function is secondary to its ability to induce Phase 2 enzymes, and it is therefore an "indirect antioxidant." The magnitude of the protective effects depends on concentrations of both oxidant stressors and inducers. Notably, unlike the effects of most direct antioxidants, the indirect antioxidant status persists for several days after sulforaphane is no longer present.

Parallel measurements of Phase 2 enzymes and GSH levels were obtained on cell extracts that had been exposed to sulforaphane under identical conditions to those used in protection experiments. When the degree of protection, quantified by increases in $D_m$ values, was compared to elevations of these Phase 2 markers, remarkably close correlations were observed. Taken together, these results establish that protection against oxidative stress is quantitatively related to the indirect antioxidant action of sulforaphane which results from elevations of Phase 2 enzymes and GSH.

Materials And Methods

Chemicals.

Tert-Butyl hydroperoxide, 3-morpholinosydnonimine (SIN-1), menadione sodium bisulfite (menadione), and 3-[4, 5-dimethylthiazol-2-yl]-2,5-diphenyl tetrazolium bromide (MTT), all-trans-retinal was purchased from Sigma (St. Louis, Mo.). 4-Hydroxynon-2-enal was obtained from Cayman Chemical Co. (Ann Arbor, Mich.), and synthetic sulforaphane [1-isothiocyanato-(4R,S)-(methylsulfinyl)butane] was from LKT Laboratories (St. Paul, Minn.).

Cell Culture.

Human adult retinal pigment epithelial cells (ARPE-19, TCC Catalog No. CRL-2302) were obtained from the American Type Culture Collection (Manassas, Va.). These cells have structural and functional properties similar to the analogous retinal cells in vivo (Dunn, K. C., Aotaki-Keen, A. E., Putkey, F. R. & Hjelmeland, L. M. (1996) *Exp. Eye Res.* 62, 155-159). They were cultured in a mixture of equal volumes of Dulbecco's modified Eagle's medium (DMEM) and Ham's F12 medium plus 10% fetal bovine serum that was heated for 90 min at 55° C. with 1% (w/v) charcoal.

Human skin keratinocytes (HaCaT) were obtained from Dr. G. Tim Bowden, Arizona Cancer Center, Tucson, Ariz.

and grown in Eagle's minimum essential medium (EMEM) plus 8% fetal bovine serum that had been treated with Chelex resin (Bio-Rad, Hercules, Calif.) to remove $Ca^{2+}$ (Boukamp, P., Petrussevska, R. T., Breitkreutz, D., Hornung, J., Markham, A. & Fawning, N. B. (1988) *J. Cell Biol.* 106, 761-771). Mouse L1210 leukemia cells, a gift from Dr. Joseph G. Cory, East Carolina State University, Greenville, N.C., were grown in RPMI 1640 medium supplemented with 10% horse serum. All cultures were incubated in a humidified atmosphere of 5% $CO_2$ at 37° C. Media and sera were obtained from Life Technologies (Rockville, Md.).

Induction of Phase 2 Response by Sulforaphane.

All experiments were performed in 96-well microliter plates. ARPE-19 and HaCaT cells were seeded at 10,000 cells per well and grown for 24 h before addition of sulforaphane, whereas L1210 cells (5,000 cells/well) were not incubated before sulforaphane treatment. Solutions of sulforaphane (5 mM) in dimethyl sulfoxide were diluted with the cognate culture medium to provide final inducer concentrations of 0.16-5.0 µM. The final DMSO concentrations were 0.1% by volume.

Choice of Oxidants.

tert-Butyl hydroperoxide differs from lipid hydroperoxides in being water-soluble, but unlike hydrogen peroxide, it is not metabolized by the peroxidative actions of catalase. It is principally inactivated by direct and glutathione transferase-promoted reduction of GSH (Hurst, R., Bao, Y., Jemth, P., Mannervik, B. & Williamson, G. (1998) *Biochem J.* 332, 97-100). Menadione causes necrotic cell death by participating in oxidative cycling which generates superoxide and more reactive oxygen species, by depletion of sulfhydryl groups, and by accumulation of toxic intracellular levels of calcium (Smith, M. T., Evans, C. G., Thor, H. & Orrenius, S. (1985) In: *Oxidative stress*, (H Sies, ed.) Academic Press, London, pp. 91-113). The relative toxicological importance of these processes probably depends on the tissue and local conditions. An important detoxification mechanism for menadione is the obligatory two-electron reduction to hydroquinones promoted by NAD(P)H: quinone reductase 1 (QR) (Dinkova-Kostova, A. T. & Talalay, P. (2000)*Free Radical Biol. Med.* 29, 231-240). Mice in whom this gene has been disrupted are much more sensitive to the toxicity of menadione (Radjendirane, V., Joseph, P., Lee, Y.-H., Kimura, S., Klein-Szanto, A. J. P., Gonzalez, F. J. & Jaiswal, A. K. (1998) *J. Biol. Chem.* 273, 7382-7389).

4-Hydroxynonenal is a highly cytotoxic and genotoxic alkenal that arises from peroxidation of polyunsaturated fatty acids such as arachidonic acid and its tissue abundance is widely used as an index of lipid peroxidation (Prior, W. A. & Porter, N. A. (1990) *Free Radical Biol. Med.* 8, 541-543; Esterbauer, H., Schauer, R. J. & Zollner, H. (1991) *Free Radical Biol. Med.* 11, 81-128). The principal pathway for detoxification of 4-hydroxynonenal is conjugation with GSH by glutathione transferases leading to mercapturic acid formation (Alary, J., Bravais, E., Cravedi, J. P., Debrauwer, L., Rao, D. & Bories, G. (1995) *Chem. Res. Toxicol.* 8, 34-39; Hubatsch, I., Ridderstrom, M. & Mannervik, B. (1998) *Biochem J.* 330, 175-179).

Peroxynitrite is a much more powerful oxidant than either superoxide or nitric oxide and is formed in cells by the exceedingly rapid combination of these molecules. Although nitric oxide can protect cells against apoptosis, peroxynitrite is a much more toxic reagent and attacks many cellular components, reacting with thiols, iron-sulfur centers, and zinc fingers, and it initiates lipid peroxidation. It also nitrates tyrosine by a reaction catalyzed by superoxide dismutase (Estévez, A. G., Spear, N., Pelluffo, H., Kamaid, A., Barbeito, L. & Beckman, J. S. (1999) *Methods Enzymol.* 301, 393-402). Peroxynitrite probably generates cellular oxidative stress by several mechanisms.

There is accumulating evidence that chronic exposure to sunlight plays a role in some degenerative diseases, for instance, age-related macular degeneration (AMD). We have, therefore, carried out an experiment of protection of human RPE cells against photooxidative damage mediated by all-trans-retinal, which exists in human retina and is a critical component of the visual cycle.

Treatment with Oxidants.

Tert-Butyl hydroperoxide (1 M) and 4-hydroxynonenal (25 mM) were dissolved in DMSO and diluted 1000-fold with serum-free medium before addition of serial dilutions to the microtiter plate wells. The final concentrations of DMSO were therefore less than 0.1% (by vol.). Menadione sodium bisulfite (0.5 M) and SIN-1 (0.5 M) were dissolved and added in PBS. ARPE-19 cells were exposed to menadione for 2 h and to tert-butyl hydroperoxide for 16 h, washed with PBS, and cell viability was determined by the MIT test. ARPE-19 cells were exposed to peroxynitrite for 2 h and 4-hydroxynonenal for 4 h, and the cells were then incubated in serum-free media for 22 and 20 h, respectively, washed with PBS, and cell viability was determined. The additional incubation periods were required for peroxynitrite and 4-hydroxynonenal to evoke maximal cytotoxicity.

Cytotoxicity Measurements.

Cell viability was determined by spectroscopic measurement of the reduction of MTT (Carmichael, J., DeGraff, W. G., Gazdar, A. F., Minna, J. D. & Mitchell, J. B. (1987) *Cancer Res.* 47, 936-942). The culture media were discarded after the designated incubation periods, the cells were washed three times with PBS by use of a microtiter plate washer (Ultrawash Plus, Dynex Technologies, Chantilly, Va.). Each well then received 150 µl of an MTT solution (0.5 mg/ml) in serum-free medium. The plates were incubated for 2 h at 37° C., the MTT solution was discarded, 100 µl of DMSO were added to each well, and the plates were shaken at 200 rpm on an orbital shaker for 5 min. The absorbances of the wells were determined at 555 nm with a microtiter plate reader (Spectra Max Plus, Molecular Devices, Sunnyvale, Calif.). The absorbance of reduced MIT was then compared at each inducer and oxidant concentration to that of untreated control cells that received only the vehicle in which sulforaphane (DMSO) and menadione (DMSO or PBS) were dissolved. In each experiment three identical 96-well plates were used and the means of the absorbance values, the standard deviations of these means, and their coefficients of variation were calculated. The coefficients of variation ranged from 0.6% to 16.5%. The mean coefficients of variation were similar for treated and untreated cells and averaged 7.2±4.2%.

Quantitative Analysis of Cytotoxicity.

Dose-effect analyses were performed according to the Median Effect Equation, by use of a computer program (Chou, T. C. & Hayball, M. (1996) *CalcuSyn for Windows* 3.1 and 95: *multiple dose effect analyzer and manual for IBM-PC*, Biosoft, Cambridge, U.K). The equation: $f_a/f_u = [D/D_m]^m$, where $f_a$ is the fraction of cells affected by the oxidant, $f_u$ is the fraction unaffected (i.e., $1-f_a$), D is the dose of oxidant required to produce the effect $f_a$, $D_m$ is the concentration of oxidant required to produce a 50% effect, i.e., when $f_a=f_u$, and the slope m is a measure of the sigmoidicity of the dose-response curve, and is therefore a measure of cooperativity. The results are analyzed by plotting $\log(f_a/f_u)$ with respect to log D of the oxidant. The computer program provides the slope (m) of the curves, and the goodness of fit ($r^2$) to linearity.

Preparation Of Cell Lysates.

Cells were lysed by addition of a digitonin solution (0.8 mg/ml digitonin in 2 mM EDTA, pH 7.8), incubated at 37° C. for 20 min, gently shaken for 20 min at 25° C., and centrifuged at 1,500×g for 20 min at 4° C.

Glutathione Analysis.

Total glutathione (oxidized and reduced) was determined by reduction of 5,5'-dithiobis-2-nitrobenzoic acid (DTNB) in a glutathione reductase-coupled assay in 96-well microliter plates (Ritchie, J. P., Jr., Skowronski, L., Abraham, P. & Leutzinger, Y. (1996) Clin. Chem. 42, 64-70). Briefly, 30 µl of lysates were mixed with 60 µl of cold 2.5% metaphosphoric acid, stored at 4° C. for 10 min, and centrifuged for 20 min at 1,500×g at 4° C. In a new plate, 50 µl of the supernatant fraction of each sample were mixed with 50 µl of 1.26 mM DTNB, 50 µl of 200 mM sodium phosphate, pH 7.5, 5 mM EDTA, and 50 µl of a solution containing 3.1 units/ml of yeast glutathione reductase (Sigma, St. Louis, Mo.). After 5 min incubation at 25° C., 50 µl of 0.72 mM NADPH were added to each well, and the initial reaction rates were determined at 412 nm. Calibration curves for pure GSH were included in each assay.

Enzyme Assays.

All measurements were made in 96-well microtiter plates at 25° C., and reaction rates were monitored with a microtiter plate reader. The QR activities of supernatant fractions were determined by procedures developed in our laboratory (Fahey, J. W., Zhang, Y. & Talalay, P. (1997) Proc. Natl. Acad. Sci. USA 94, 10367-10372; Prochaska, H. J., Santamaria, A. B. & Talalay, P. (1992) Proc. Natl. Acad. Sci. USA 89, 2394-2398.). Specific activities were obtained by relating the reaction rates to protein concentrations determined with the bicinchoninic acid reagent (Smith, P. K., Krohn, R. I., Hermanson, G. T., Mallia, A. K., Gratner, F. H., Provenzano, M. D., Fujimoto, E. K., Goeke, N. M., Olson, B. J. & Klenk, D. C. (1985) Anal. Biochem. 150, 76-85). The dicumarol-inhibitable fraction of the total QR activity contributed more than 90% to the overall observed rates in the ARPE-19, HaCaT, and L1210 cells. Glutathione reductase activity was assayed by mixing 50 µl of cell lysate with 25 µl of 1 mM NADPH, 25 µl of GSSG (20 mg/ml), and 150 µl of 50 mM sodium phosphate, pH 7.5. Initial reaction rates were obtained at 340 nm (Carlberg, I. & Mannervik, B. (1985) Methods Enzymol. 113, 484-490). Glucose 6-phosphate dehydrogenase was assayed by mixing 50 µl of cell lysate with 200 µl of assay buffer containing 2.0 mM glucose 6-phosphate, 20 mM $MgCl_2$, and 150 µM NADP. Initial reaction rates were determined at 340 nm (Kornberg, A. & Horecker, B. L. (1955) Methods Enzymol. 1, 323-327).

Example 1

Quantitative Measurements of Menadione Toxicity to Human Retinal Pigment Epithelial Cells and Protection by Sulforaphane A standardized, highly reproducible system for quantitative determination of oxidant toxicity and protection by sulforaphane was developed for ARPE-19 cells grown in 96-well microtiter plates. The protective effect of 24 h prior incubation with 0-5 µM concentrations of sulforaphane on survival of ARPE-19 cells exposed for 2 h to 0-250 µM menadione is illustrated in FIG. 1, which shows the S-shaped dependence of cytotoxicity on increasing concentrations of menadione (plotted as the fractional cell kill, or fraction affected=$f_a$). At the highest concentration of menadione almost no cells survive, but prior treatment with sulforaphane protected a substantial fraction of cells against oxidative death. Over the concentration ranges examined, cell survival decreases as the concentration of the oxidant menadione is increased, and increases as the concentration of sulforaphane is raised, as shown in the photograph (FIG. 1).

Analysis of the data by the median effect equation of Chou & Talalay, (1984) Adv. Enzyme Regul. 22, 27-55, provides: (a) a measure of the toxicity of the oxidant under each set of experimental conditions, expressed as the median effect concentration ($D_m$); (b) compliance of the data with mass action principles that underlie the theoretical basis of the median effect equation i.e., the magnitudes of $r^2$ values of plots of log $[f_a/f_u]$ with respect to log D; and (c) the Hill type coefficient (m), a measure of the sigmoidicity of the curves and hence of the cooperativity between the processes contributing to the biological endpoint (cell death). The median effect plots of the above data (FIG. 1) are a family of parallel and linear graphs (average of $r^2$ for 5 plots=0.976±0.016) with average slopes (m) of 3.44±0.22 (Table 1, shown below). These high slopes suggest that the processes contributing to cytotoxicity of menadione are highly cooperative. Notably, the $D_m$ values rise asymptotically from 72.2 µM menadione under basal conditions to 134.2 µM for cells that had been treated with 5 µM sulforaphane for 24 h. In two other experiments, carried out at intervals of many weeks, the control $D_m$ values were 65.0 and 69.0 µM, respectively, and were therefore in good agreement.

Table 1 also shows results from experiments in which ARPE-19 cells, HaCaT cells or L1210 cells were treated with the Menadione, tert-Butyl hydroperoxide, 4-hydroxynonenal, or peroxynitrite. The viability of the cells was determined by the MTT reduction measurements under conditions described above. $D_m$ values were obtained from a series of plots of log($f_a/f_u$) with respect to log oxidant concentration at each concentration of sulforaphane. The m values are the slopes of these plots and $r^2$ the linear correlation coefficients.

TABLE 1

Analysis by Median Effect Equation of protection by sulforaphane of human retinal pigment epithelial cells (ARPE-19), keratinocytes (HaCaT), and murine leukemia (L 1210) cells, against the toxicities of menadione, tert-butyl hydroperoxide, 4-hydroxynonenal and peroxynitrite

| Oxidants | Sulforaphane (µM) | $D_m$ (µM) | m | $r^2$ |
|---|---|---|---|---|
| ARPE-19 cells | | | | |
| Menadione | 0.00 | 72.2 | 3.35 | 0.952 |
|  | 0.63 | 98.6 | 3.69 | 0.979 |
|  | 1.25 | 110 | 3.49 | 0.983 |
|  | 2.50 | 123 | 3.58 | 0.994 |
|  | 5.00 | 134 | 3.12 | 0.972 |
| tert-Butyl hydroperoxide | 0.00 | 95.8 | 2.52 | 0.923 |
|  | 0.63 | 140 | 2.17 | 0.964 |
|  | 1.25 | 163 | 1.79 | 0.980 |
|  | 2.50 | 165 | 1.26 | 0.953 |
| 4-hydroxynonenal | 0.00 | 8.70 | 2.85 | 0.885 |
|  | 0.63 | 14.1 | 2.51 | 0.931 |
|  | 1.25 | 25.8 | 2.78 | 0.981 |
|  | 2.50 | 26.8 | 2.51 | 0.993 |
| Peroxynitrite | 0.00 | 1440 | 6.07 | 0.958 |
|  | 0.63 | 2780 | 6.30 | 0.984 |
|  | 1.25 | 2820 | 6.19 | 0.982 |
|  | 2.50 | 2890 | 6.62 | 0.977 |
| HaCaT cell | | | | |
| tert-Butyl hydroperoxide | 0.00 | 63.5 | 0.899 | 0.955 |
|  | 0.63 | 113 | 0.894 | 0.965 |

TABLE 1-continued

Analysis by Median Effect Equation of protection by sulforaphane of human retinal pigment epithelial cells (ARPE-19), keratinocytes (HaCaT), and murine leukemia (L 1210) cells, against the toxicities of menadione, tert-butyl hydroperoxide, 4-hydroxynonenal and peroxynitrite

| Oxidants | Sulforaphane (µM) | $D_m$ (µM) | m | $r^2$ |
|---|---|---|---|---|
|  | 1.25 | 166 | 0.921 | 0.971 |
|  | 2.50 | 200 | 0.768 | 0.974 |
|  |  | L1210 cell |  |  |
| Menadione | 0.00 | 12.2 | 0.725 | 0.967 |
|  | 0.16 | 19.6 | 0.864 | 0.986 |
|  | 0.31 | 26.5 | 1.00 | 0.987 |
|  | 0.63 | 36.2 | 1.17 | 0.977 |

Example 2

Figure 2:
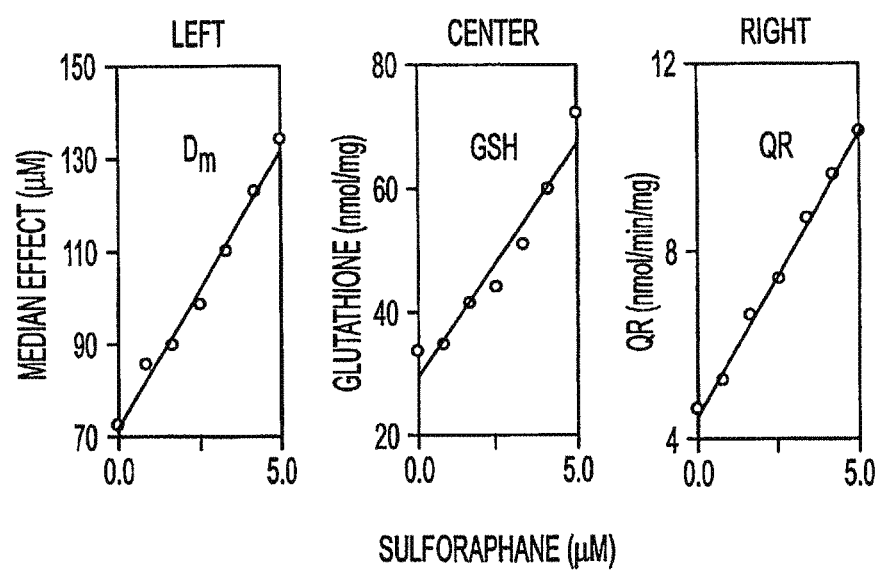
FIG. 2. Comparison of the effects of treatment of human ARPE-19 cells with a series of concentrations of sulforaphane (0-5 µM) for 24 h on the toxicity of exposure for 2 h to menadione. Left, cytotoxicity expressed as the median effect concentration ($D_m$). Center, glutathione concentrations expressed as nanomol/mg of cytosolic protein. Right, quinone reductase specific activity, expressed as nanomol/min/mg of cytosolic protein. The multivariate regression correlations between sulforaphane concentrations and the other three variables all had p values of <0.01.

Correlation Between Protection of ARPE-19 Against Menadione Toxicity by Sulforaphane and Elevations of Glutathione Levels and Quinone Reductase Specific Activities The specific activities of QR and concentrations of GSH were measured in cytosols of ARPE-19 cells that had been treated with 0-5.0 µM sulforaphane for 24 h, under conditions identical to those used above to determine the $D_m$ values for menadione toxicity. As expected, both indicators of Phase 2 induction rose with exposure to increasing concentrations of sulforaphane (FIG. 2). The responses were linearly correlated with the sulforaphane concentration ($r^2$=0.995 and 0.935, respectively). More importantly, a multivariate regression analysis showed a highly correlation between sulforaphane concentrations and QR activities, GSH levels and $D_m$ values (p=0.0095, 0.0004, 0.0038, respectively). There is therefore a highly significant quantitative association between the degree of protection afforded by sulforaphane against menadione toxicity and the elevations of QR activities and GSH levels, suggesting strongly that the changes in these variables are causally related.

Example 3

Sulforaphane Provides Prolonged Antioxidant Protection Against Menadione Oxidant Stress Since sulforaphane, like other isothiocyanates, does not normally participate in oxidation/reduction reactions, its antioxidant mechanism must be indirect, presumably through induction of Phase 2 proteins. Consequently, it seemed likely that the protective effects of sulforaphane should be catalytic and persist for several days (in relation to the half-lives of the cognate proteins) after removal of the inducer, unlike direct antioxidants (e.g., ascorbic acid, tocopherols) which are consumed stoichiometrically in radical quenching reactions. Therefore ARPE-19 cells were treated for 24 h with two concentrations of sulforaphane (0.625 and 2.5 µM) and then incubated them for an additional 96 h in medium without fetal bovine serum (in order to minimize the complications of cell growth and the difficulties of distinguishing the effects of cell mass increases on specific biochemical indices). Triplicate sets of identical plates were evaluated for menadione toxicity (2-h exposure) immediately after sulforaphane exposure and at 24-h intervals thereafter. The median effect concentration ($D_m$) for menadione of control cells was 66.8 µM and the $D_m$ values for cells treated with 0.625 and 2.5 µM sulforaphane were 69.2 and 94.5 µM, respectively. Control cell resistance remained unchanged for 48 h, whereas the resistance to menadione toxicity of the cells treated with sulforaphane continued to increase during this period, and then declined over the subsequent 48 h, finally approaching control cell levels (FIG. 3).

Figure 3:
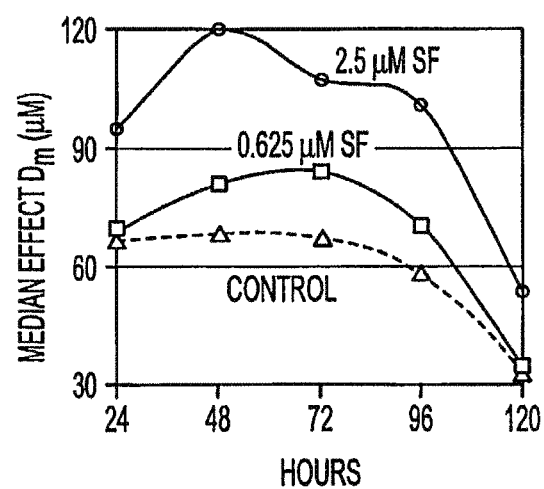
FIG. 3. Prolonged protection of ARPE-19 cells against menadione toxicity by sulforaphane (SF) expressed as median effect concentrations ($D_m$, µM). The menadione toxicity was determined immediately after induction (time=0), and 24, 48, 96 and 120 h later. Note that protection continued to rise for 24-48 h, and then declined during the next 48 h.
Figure 4:
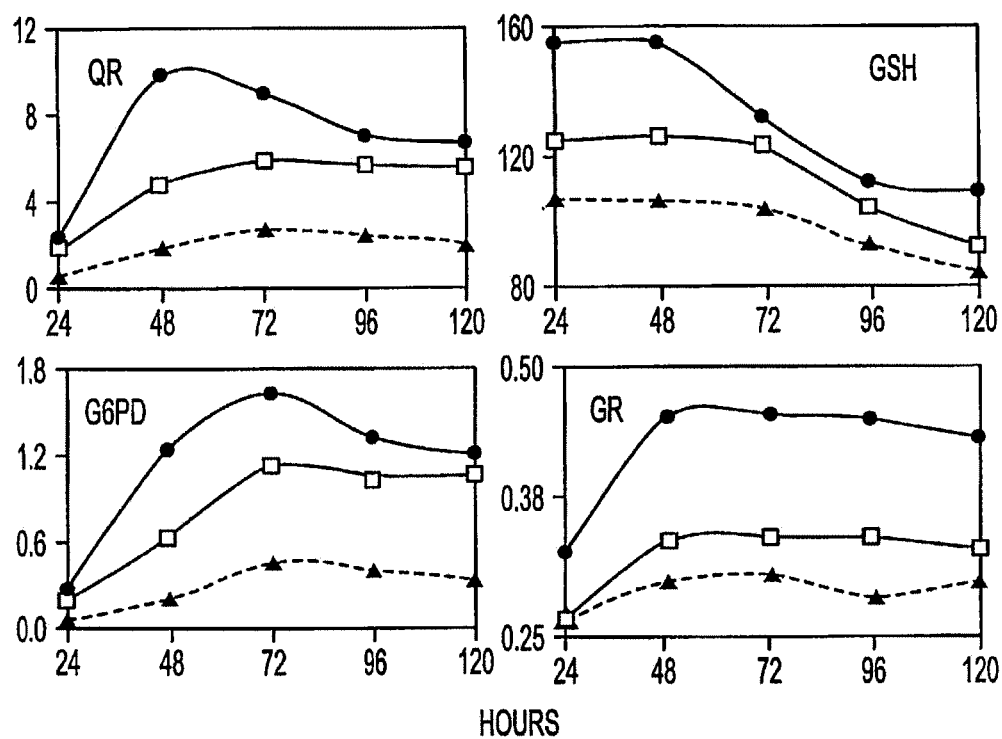
FIG. 4. Persistent induction of quinone reductase (QR), glucose 6-phosphate dehydrogenase (G6PD), glutathione reductase (GR) (nanomol/min/mg of cytosolic protein) and elevation of GSH levels (expressed as nanomol/mg of cytosolic protein) in human ARPE-19 cells after exposure to sulforaphane for 24 h[0,0 (▲), 0.625 (□) and 2.5 µM (●)].

These experiments establish that the protection evoked by sulforaphane at the end of the 24-h induction treatment is maintained or exceeded for at least 3 days in culture (FIG. 3). The specific activities of QR, glucose 6-phosphate dehydrogenase, and glutathione reductase in the cytosols of cells treated in an identical manner also continued to rise for 48 h after removal of sulforaphane from the medium and then remained high (glucose 6-phosphate dehydrogenase and glutathione reductase) or declined modestly (QR) over the ensuing 48-72 h (FIG. 4). The GSH levels after 24 h treatment with 2.5 µM sulforaphane were increased about 50%, remained at this level for another 24 h, and then declined to control cell levels in the ensuing 96 h. Notably, in ARPE-19 cells that have been exposed to sulforaphane for 24 h, and are then maintained in serum-free culture media for several days, the protective status remains substantially elevated, in parallel with higher levels of GSH and elevated Phase 2 enzyme markers.

Example 4

Figure 5:
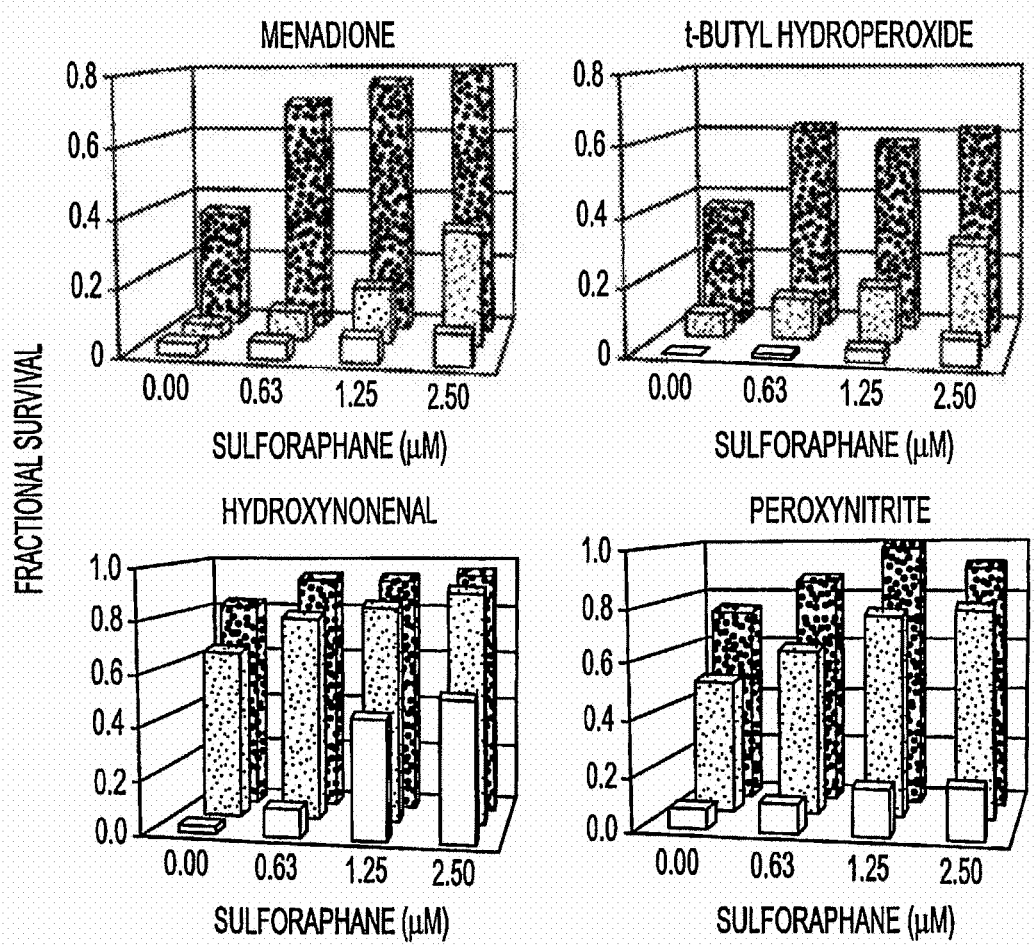
FIG. 5. Protection of human ARPE-19 cells against the toxicity of menadione (62, 125, 200 µM for 2 h), tert-butyl hydroperoxide (0.5, 0.75, 1 mM for 16 h), 4-hydroxynonenal (6.25, 12.5, 25 µM for 4 h), and peroxynitrite (1, 2, 4 mM for 2 h) as a function of prior exposure for 24 h to 0-2.5 µM sulforaphane. The bar graphs show that cell viability is a function of both the concentrations of the oxidant and of the sulforaphane inducer. The front, center and rear series of bars refer to the highest, middle and lowest concentration of oxidants, respectively.

Protection of ARPE-19 Cells by Sulforaphane Against the Oxidative Stress of Tert-Butyl Hydroperoxide, Peroxynitrite, and 4-Hydroxynonenal by Sulforaphane Treatment of ARPE-19 cells with a range of concentrations of sulforaphane (0, 0.625, 1.25, and 2.5 mM) for 24 h, also provided protection against other oxidants with mechanisms of action that differed from that of menadione. Thus the cytotoxicities of tert-butyl hydroperoxide (0.5-1.0 mM for 16 h), peroxynitrite (generated from SIN-1, 0.25-4.0 mM for 2 h), and 4-hydroxynonenal (1.56-25 µM for 4 h) were also significantly ameliorated by treatment with sulforaphane. This protection, like that against menadione, depended on concentration of both the oxidants and sulforaphane (FIG. 5 and Table 1).

More detailed examination of the protective effects by the median effect equation reveals: (a) the slopes m for the cytotoxicities of these oxidants are quite different (means of 1.93, 2.66, and 6.29 for tert-butyl hydroperoxide, 4-hydroxynonenal, and peroxynitrite, respectively), and different from the m value (3.45) for menadione; and (b) the degree of protection provided by comparable concentrations of sulforaphane against different antioxidants ranged from 2- to 3-fold.

Example 5

Figure 6:
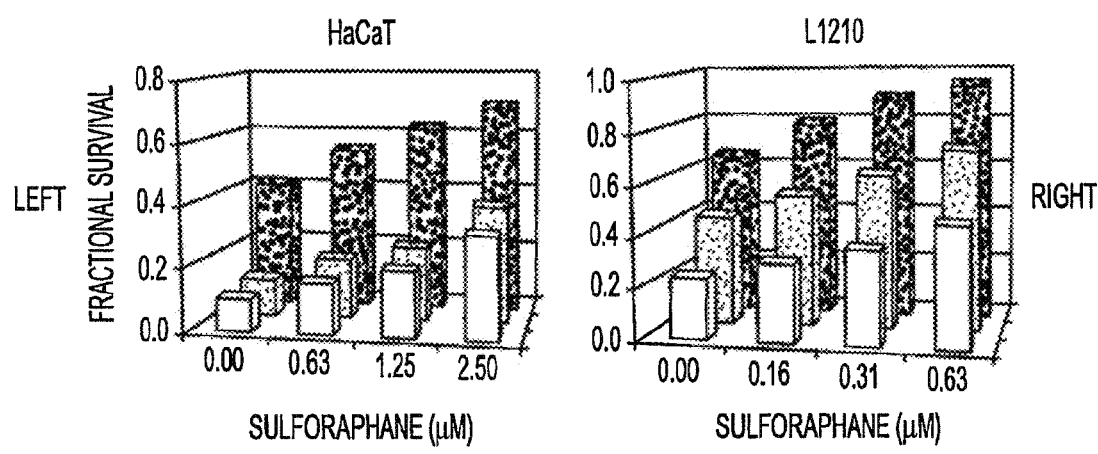
FIG. 6. Protection of human keratinocytes (HaCaT) against oxidative cytotoxicity of tert-butyl hydroperoxide (0.313, 0.625, 1 mM for 8 h) (left), and mouse leukemia (L1210) cells against oxidative cytotoxicity of menadione (15.6, 31.3, 62.5 µM for 2 h) (right) by treatment with sulforaphane (0-2.5 µM for 24 h). The $D_m$ and m values obtained from the median effect plots are shown in Table 1. The front, center and rear series of bars refer to the highest, middle and lowest concentration of oxidants, respectively.

Protection of Human Keratinocytes (HaCaT) and Murine Leukemia (L1210) Cells Against Oxidative Stress To examine the generality of protection by Phase 2 induction an analysis of the effects of 24 h treatment with sulforaphane on the toxicity to human keratinocytes (HaCaT) and mouse leukemia (L1210) cells of tert-butyl hydroperoxide and menadione, respectively (FIG. 6) was conducted. Interestingly, the slopes of the median effect plots for both oxidants in these cell lines are in the 0.8-1.2 range, indicating lack of significant cooperativity among the processes contributing to cell death in these cell lines. This is quite different from the effects of the same oxidants on ARPE-19 cells (Table 1). It appears therefore that the cooperativity between lethal processes depends on the cell line. Nevertheless, the substantial protection observed in the untransformed human keratinocyte cell line and in the highly neoplastic murine leukemia cell line indicates that the protection provided by sulforaphane is a more general phenomenon, not restricted to retinal epithelial pigment cells.

Example 6

Protection of Human ARPE Cells Against the Photo-Oxidative Attack Induced by all-Trans-Retinal and Light Exposure at 365 Nm To examine the protective effect of sulforaphane against photooxidative damage mediated by all-trans-retinal and light exposure, the cells were treated with 0-100 μM of all-trans-retinal for 2 hours and light exposure at 365 nm for 20 min after incubation with 0-5 μM of sulforaphane for 24 hours. Table 2 shows that cell viability is a function of the concentrations of the photo-oxidants and of the sulforaphane. For instance, the cell viability (9.4, 11.7, 15.2 and 27.4% of the control) was dependent on the concentration of sulforaphane (0.0, 1.25, 2.5 and 5.0 μM respectively) when the cells were treated with 50 μM all-trans-retinal.

TABLE 2

Survival (%) of Retina Pigment Epithelium Cell Exposed to All-trans-Retinal in light and dark and pretreated with Sulforaphane

| Sulforaphane (μM) | All-trans-Retinal (μM) | | | | | |
|---|---|---|---|---|---|---|
| | 100 | 50 | 25 | 12.5 | 0 | Control |
| Exposed to 365 nm light | | | | | | |
| 0.00 | 3.1 | 9.4 | 41.9 | 83.6 | 100.6 | 100.5 |
| 1.25 | 3.4 | 11.7 | 54.4 | 95.4 | 100.0 | 100.7 |
| 2.50 | 5.2 | 15.2 | 63.8 | 96.5 | 100.6 | 97.4 |
| 5.00 | 8.2 | 27.4 | 72.2 | 103.4 | 100.4 | 101.4 |
| In Dark | | | | | | |
| 0.00 | 75.0 | 96.8 | 97.6 | 96.3 | 97.1 | 99.1 |
| 1.25 | 74.7 | 98.4 | 97.7 | 96.3 | 96.6 | 96.7 |
| 2.50 | 75.6 | 99.9 | 98.3 | 101.5 | 99.4 | 99.5 |
| 5.00 | 84.6 | 106.8 | 104.8 | 104.6 | 103.1 | 105.6 |

What is claimed:

1. A method of treating a subject in need of treatment of an oxidative stress disorder, said method comprising administering to said subject a composition comprising an effective amount of a compound that elevates intracellular levels of glutathione or intracelluar levels of at least one Phase IT detoxification enzyme in diseased tissue of said subject, wherein said oxidative stress disorder is selected from the group consisting of Alzheimer's Disease and aging.

2. The method of claim 1, wherein said compound is selected from the group consisting of an isothiocyanate and a glucosinolate.

3. The method of claim 2, wherein said isothiocyante is sulforaphane.

4. The method of claim 1, wherein said Phase IT detoxification enzyme is selected from the group consisting of UDP-glucuronosyltransferases, sulfotransferases, phenol-O-methyltransferase, catechol-O-methyltransferase, histamine N-methyltransferase, nicotinamide N-methyltransferase, thiopurine methyltransferase, thiol methyltransferase, N-acetyltransferases, O-acetyltransferases, acyl-CoA synthetases, acyl-CoA:amino acid N-acyltransferases, aminoacyl-tRNA synthetases, glutathione synthetases, gamma glutamylcysteine synthetases, glutathione S-transferases, quinone reductases, heme oxygenases, rhodaneses, glutathione reductase, glutathione peroxidase, catalase and superoxide dismutase.

5. A method of protecting a subject from an oxidative stress disorder, said method comprising administering to said subject a composition comprising an effective amount of a compound that elevates intracellular levels of glutathione or intracellular levels of at least one Phase II detoxification enzyme in diseased tissue of said subject, wherein said oxidative stress disorder is selected from the group consisting of Alzheimer's Disease and aging.

6. The method of claim 5, wherein said compound is selected from the group consisting of an isothiocyanate and a glucosinolate.

7. The method of claim 6, wherein said isothiocyanate is sulforaphane.

8. The method of claim 5, wherein said Phase II detoxification enzyme is selected from the group consisting of UDP-glucuronosyltransferases, sulfotransferases, phenol-O-methyltransferase, catechol-O-methyltransferase, histamine N-methyltransferase, nicotinamide N-methyltransferase, thiopurine methyltransferase, thiol methyltransferase, N-acetyltransferases, O-acetyltransferases, acyl-CoA synthetases, acyl-CoA:amino acid N-acyltransferases, aminoacyl-tRNA synthetases, glutathione synthetases, gamma glutamylcysteine synthetases, glutathione S-transferases, quinone reductases, heme oxygenases, rhodaneses, glutathione reductase, glutathione peroxidase, catalase and superoxide dismutase.

9. The method of claim 1, wherein the composition is administered orally, nasally, parenterally, intrasystemically, intraperitoneally, topically, bucally, or as an oral or nasal spray.

10. The method of claim 1, wherein the composition further comprises a carrier or excipient and is formulated as a lotion, a cream, a gel or an ointment for topical administration.

11. The method of claim 10, wherein the composition is administered to the skin.

12. The method of claim 5, wherein the composition is administered orally, nasally, parenterally, intrasystemically, intraperitoneally, topically, bucally, or as an oral or nasal spray.

13. The method of claim 5, wherein the composition further comprises a carrier or excipient and is formulated as a lotion, a cream, a gel or an ointment for topical administration.

14. The method of claim 13, wherein the composition is administered to the skin.

* * * * *

UNITED STATES PATENT AND TRADEMARK OFFICE
CERTIFICATE OF CORRECTION

PATENT NO. : 8,709,406 B2
APPLICATION NO. : 13/670161
DATED : April 29, 2014
INVENTOR(S) : Xiangqun Gao et al.

Page 1 of 1

It is certified that error appears in the above-identified patent and that said Letters Patent is hereby corrected as shown below:

IN THE CLAIMS

In column 19, line 52, in claim 1, please replace "IT" with -- "II" --

In column 20, line 1, in claim 4, please replace "IT" with -- "II" --

Signed and Sealed this
Twenty-ninth Day of July, 2014

Michelle K. Lee
*Deputy Director of the United States Patent and Trademark Office*